US011413036B2

United States Patent
Goto et al.

(10) Patent No.: US 11,413,036 B2
(45) Date of Patent: Aug. 16, 2022

(54) SUTURE LOCKING DEVICE AND METHOD OF LOCKING THREAD

(71) Applicant: OLYMPUS CORPORATION, Tokyo (JP)

(72) Inventors: Osamu Goto, Tokyo (JP); Takayuki Hatanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 84 days.

(21) Appl. No.: 16/594,137

(22) Filed: Oct. 7, 2019

(65) Prior Publication Data
US 2020/0029958 A1 Jan. 30, 2020

Related U.S. Application Data

(63) Continuation of application No. PCT/JP2017/015367, filed on Apr. 14, 2017.

(51) Int. Cl.
*A61B 17/04* (2006.01)
*A61B 17/00* (2006.01)

(52) U.S. Cl.
CPC ...... *A61B 17/0487* (2013.01); *A61B 17/0469* (2013.01); *A61B 2017/0034* (2013.01); *A61B 2017/0488* (2013.01)

(58) Field of Classification Search
CPC ............ A61B 17/0487; A61B 17/0469; A61B 2017/0034; A61B 2017/0488; A61B 2090/037
See application file for complete search history.

(56) References Cited

U.S. PATENT DOCUMENTS

| | | | |
|---|---|---|---|
| 5,569,274 A * | 10/1996 | Rapacki | A61B 17/00234 128/898 |
| 5,817,111 A | 10/1998 | Riza | |
| 8,157,824 B2 * | 4/2012 | Kimura | A61B 17/1222 606/157 |
| 8,900,254 B2 * | 12/2014 | Kobayashi | A61B 17/1285 606/142 |
| 2007/0270907 A1 | 11/2007 | Stokes et al. | |
| 2013/0218175 A1 | 8/2013 | Auerbach et al. | |

OTHER PUBLICATIONS

English translation of International Preliminary Report on Patentability dated Oct. 24, 2019, together with the Written Opinion received in related International Application No. PCT/JP2017/015367.
International Search Report dated Jul. 4, 2017 issued in PCT/JP2017/015367.
Chinese Office Action dated Jan. 28, 2022 received in 201780089523.

* cited by examiner

*Primary Examiner* — Julian W Woo
(74) *Attorney, Agent, or Firm* — Scully, Scott, Murphy & Presser, P.C.

(57) ABSTRACT

A locking member of a suture locking device includes a loop portion formed in an α-shape when viewed from a width direction, and a pair of extensions extending from the loop portion towards a distal side, and an intersection portion in which the pair of extensions intersect is formed at a distal end of the loop portion. The loop portion is inserted into the hollow portion from the distal side with the thread being inserted through an inner space of loop portion, and the thread is pulled from a proximal side towards the intersection portion in the inner space of the loop portion so that the thread is locked to the loop portion.

12 Claims, 8 Drawing Sheets

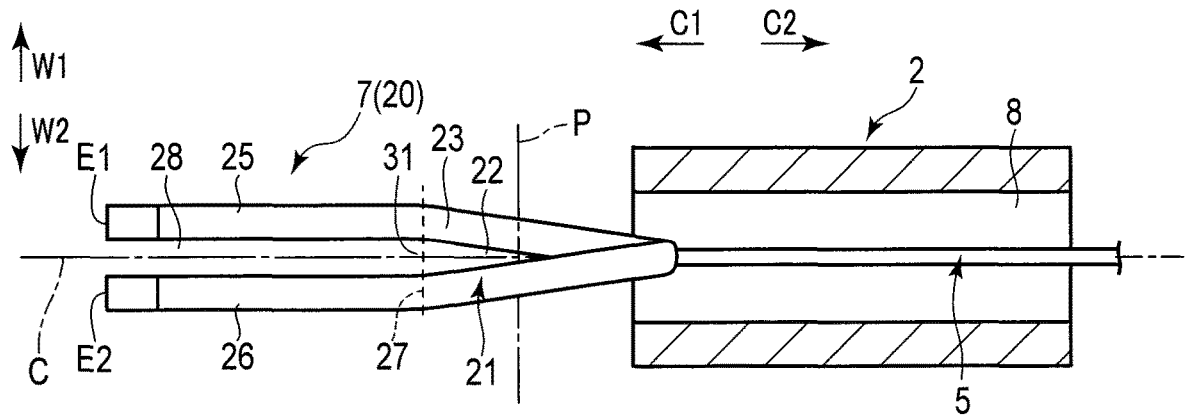
F I G. 3
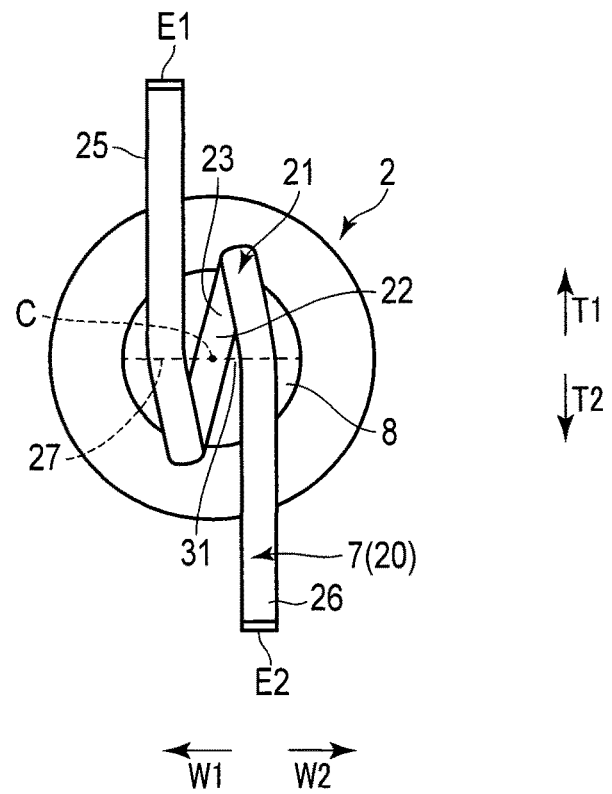
F I G. 4

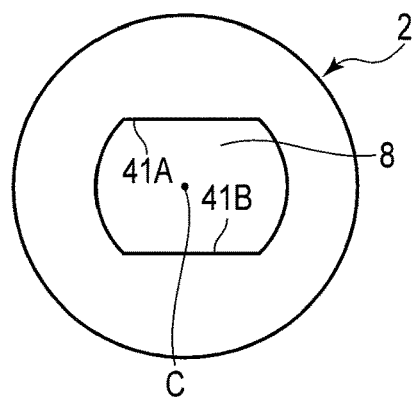
F I G. 14
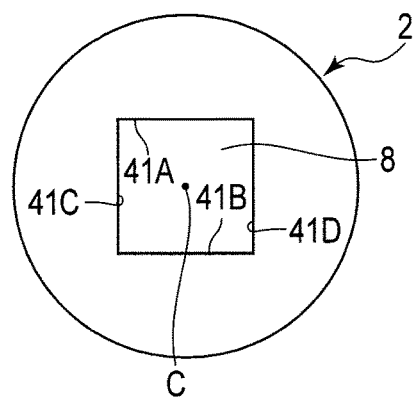
F I G. 15
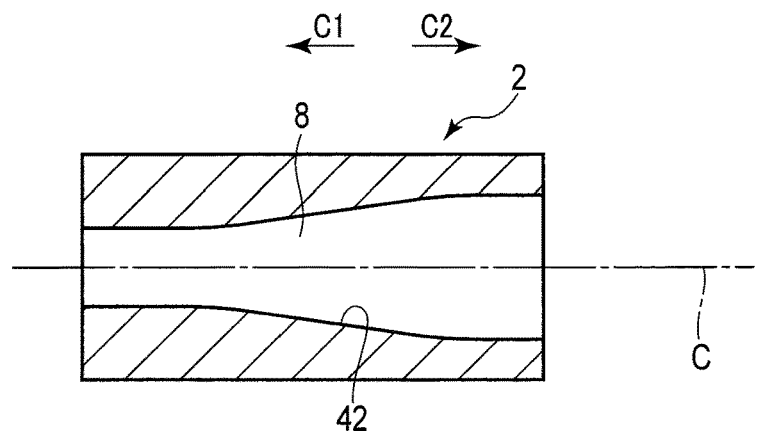
F I G. 16

SUTURE LOCKING DEVICE AND METHOD OF LOCKING THREAD

CROSS-REFERENCE TO RELATED APPLICATIONS

This is a Continuation Application of PCT Application No. PCT/JP2017/015367, filed Apr. 14, 2017, the entire contents of which are incorporated herein by reference.

BACKGROUND OF THE INVENTION

1. Field of the Invention

The present invention relates to a suture locking device for locking a suture in treatment and a method of locking a thread using this suture locking device.

2. Description of the Related Art

US 2007/0270907A1 discloses a suture locking device for locking a suture during treatment. This suture locking device is provided with an outer locking member, an inner locking member movable in a direction along a longitudinal axis relative to the outer locking member, and a cable (wire member) having its distal end connected to the inner locking member. Further, the inner locking member is formed with an inner cavity. This inner cavity opens to an outside of the inner locking member at a distal opening on the distal surface of the inner locking member and an outer peripheral opening on the outer peripheral surface of the inner locking member. A thread (suture) having sutured living tissues etc. is inserted into the inner cavity of the inner locking member from the distal opening and drawn out of the inner locking member from the inner cavity through the outer peripheral opening. The cable is then pulled toward the proximal side with the thread running through the inner cavity, and the inner locking member is inserted into the outer locking member. Portion of the thread extending from the outer peripheral opening is thereby interposed between the outer peripheral surface of the inner locking member and the inner peripheral surface of the outer locking member. Sandwiching the thread between the inner locking member and the outer locking member locks the thread by the friction between the thread and the inner locking member and the friction between the thread and the outer locking member. The thread is thus fixed to the inner locking member and the outer locking member.

BRIEF SUMMARY OF THE INVENTION

According to one aspect of the invention, a suture locking device including: a pressing tube extending along a longitudinal axis from a proximal side to a distal side, a hollow portion being formed inside the pressing tube; and a locking member having elasticity, the locking member including: a loop portion forming a proximal end of the locking member, and formed in an α-shape when viewed from a width direction intersecting with a direction along the longitudinal axis; a first extension extending from the loop portion towards the distal side, and including a distal end formed by one extension end of the locking member; and a second extension extending from the loop portion towards the distal side, and including a distal end formed by another extension end of the locking member, the second extension forming an intersection portion that intersects with the first extension at a distal end of the loop portion when viewed from the width direction, the loop portion being configured to be inserted into the hollow portion from the distal side towards the proximal side along the longitudinal axis with the thread being inserted through an inner space surrounded by the loop portion, and the pressing tube being configured to press the loop portion to an inner peripheral side of the pressing tube towards the longitudinal axis, so that the thread is pulled from the proximal side towards the intersection portion in the inner space of the loop portion and the thread is locked to the loop portion.

According to one another aspect of the invention, a method of locking a thread using a suture locking device, the suture locking device including, a pressing tube extending along a longitudinal axis from a proximal side to a distal side, a hollow portion being formed inside the pressing tube, a locking member having elasticity, and extending in an α-shape when viewed from a width direction intersecting with a direction along the longitudinal axis, a loop portion forming a proximal end of the locking member, and formed in a ring-shape when viewed from the width direction, a first extension extending from the loop portion to the distal side in the locking member, and including a distal end formed by one extension end of the locking member, and a second extension extending from the loop portion to the distal side in the locking member, and including a distal end formed by another extension end of the locking member, the second extension forming an intersection portion intersecting with the first extension at a distal end of the loop portion when viewed from the width direction, the method including: inserting the thread into an inner space surrounded by the loop portion with the loop portion protruding from a distal end of the pressing tube to the distal side; inserting the loop portion into the hollow portion of the pressing tube from the distal side towards the proximal side along the longitudinal axis with the thread inserted into the inner space of the loop portion, and pressing the loop portion to an inner peripheral side of the pressing tube towards the longitudinal axis by the pressing tube; and moving the locking member to the proximal side in the hollow portion with the thread inserted into the inner space of the loop portion, and pulling the thread from the proximal side towards the intersection portion in the inner space of the loop portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a schematic view of the locking member, the pressing tube, and the wire member according to the first embodiment, as viewed from one side in a thickness direction of the locking member, FIG. 4 is a schematic view of the locking member, the pressing tube, and the wire member according to the first embodiment, as viewed from a distal side, FIG. 14 is a schematic view of a pressing tube according to a first modification as viewed from a distal side, FIG. 15 is a schematic view of a pressing tube according to a second modification as viewed from a distal side, FIG. 16 is cross-sectional view schematically showing a pressing tube according to a third modification in a cross section substantially parallel to the longitudinal axis.

DETAILED DESCRIPTION OF THE INVENTION

First Embodiment

Figure 1:
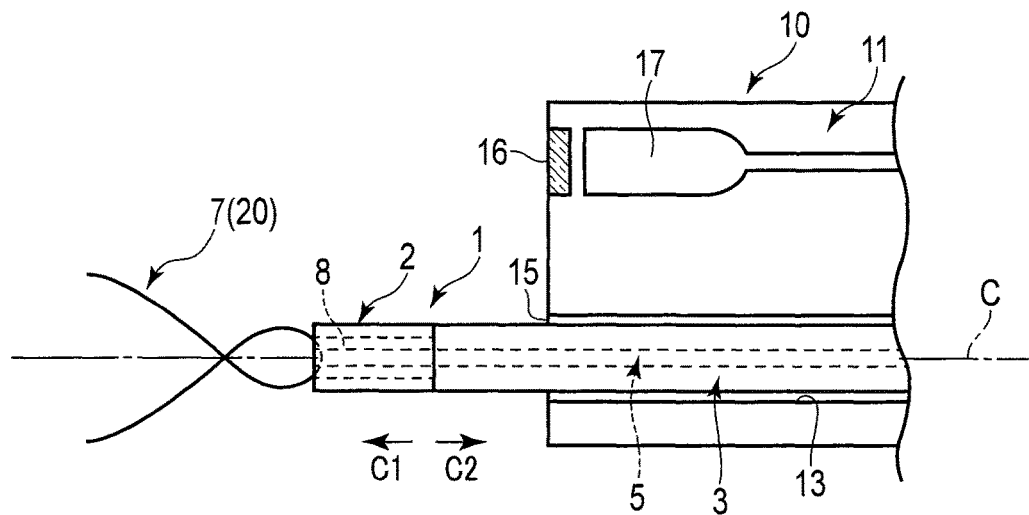
FIG. 1 is a schematic view of one example of a suture locking device according to a first embodiment and how this suture locking device may be used.

FIGS. 1 to 13 will be referenced to explain a first embodiment of the present invention. FIG. 1 is a schematic view of one example of a suture locking device 1 according to the first embodiment and how this suture locking device may be used. As shown in FIG. 1, the suture locking device 1 includes a pressing tube 2. The pressing tube 2 includes a longitudinal axis C as a central axis. One side of a direction along the longitudinal axis C is a distal side (arrow C1), and a proximal side (arrow C2) is a side opposite from the distal side. The pressing tube 2 is formed from metal or resin, and extends along the longitudinal axis C from the proximal side to the distal side. Further, an interior of the pressing tube 2 is formed with a hollow portion 8. In the present embodiment, a cross-sectional shape substantially perpendicular to the longitudinal axis C of the hollow portion 8 is formed to be a substantially circular shape.

The suture locking device 1 includes a coil sheath 3 where the pressing tube 2 abuts from the distal side. The pressing tube 2 is provided to be separable from the coil sheath 3. In the state where the pressing tube 2 abuts the coil sheath 3, the pressing tube 2 becomes substantially coaxial with the coil sheath 3, and a central axis of the coil sheath 3 is substantially coaxial with the longitudinal axis C of the pressing tube 2. The dimension of the coil sheath 3 in a direction along the central axis (longitudinal axis C) is significantly larger than the dimension of the pressing tube 2 in a direction along the longitudinal axis C. Therefore, when the pressing tube 2 abuts the coil sheath 3, the pressing tube 2 is provided on a distal portion of the coil sheath 3. When the pressing tube 2 abuts the coil sheath 3, an inside of the coil sheath 3 communicates with the hollow portion 8 of the pressing tube 2.

The proximal side of the coil sheath 3 is connected to a held section (not shown) adapted to be held by the operator etc. In the interior of the coil sheath 3, a wire member (cable) 5 extends along the central axis (longitudinal axis C) of the coil sheath 3. The wire member 5 passes through the interior of the coil sheath 3 and the hollow portion 8 of the pressing tube 2 from an inside of the held section, and extends towards the distal side. The distal end of the wire member 5 is connected to a locking member 7. The locking member 7 is formed from a constitution member 20 having elasticity. The constitution member 20 is for example, a band member and formed from metal or resin. Further, the constitution member 20 is a thin elongated member.

The suture locking device 1 is used together with, for example, an endoscope 10. Similar to a known endoscope, the endoscope 10 includes an operation section (not shown) and an insertion section 11, and a channel 13 extends from an interior of the operation section through an interior of the insertion section 11 in the endoscope 10. An insertion opening (not shown) to the channel 13 is formed in an outer surface of the operation section, and in a distal portion of the insertion section 11, an opening 15 where the channel 13 opens to an outside of the insertion section 11 is formed. When using the suture locking device 1, the locking member 7, pressing tube 2 and coil sheath 3 are inserted into the channel 13 from the insertion opening. The suture locking device 1 is used while the coil sheath 3 is inserted through channel 13 and the pressing tube 2 and the locking member 7 protrude to the exterior of the insertion section 11 from the opening 15. An imaging element 17 observes a subject through an observation window 16 provided on the distal portion of the insertion section 11, and light is irradiated through a lighting window (not show) provided on the distal portion of the insertion section 11.

The coil sheath 3 and the wire member 5 are used as an applicator for inserting the suture locking device 1 into a body cavity through the channel 13 of the endoscope 10. For the suture locking device 1 to be inserted through the channel 13 of the endoscope 10, the suture locking device 1 may be attached to the distal portions of the coil sheath 3 and the wire member 5 in advance. Or, a surgeon etc. may attach the suture locking device 1 to the distal portions of the coil sheath 3 and the wire member 5 immediately before the suture locking device 1 is inserted through the channel 13 of the endoscope 10.

Figure 2:
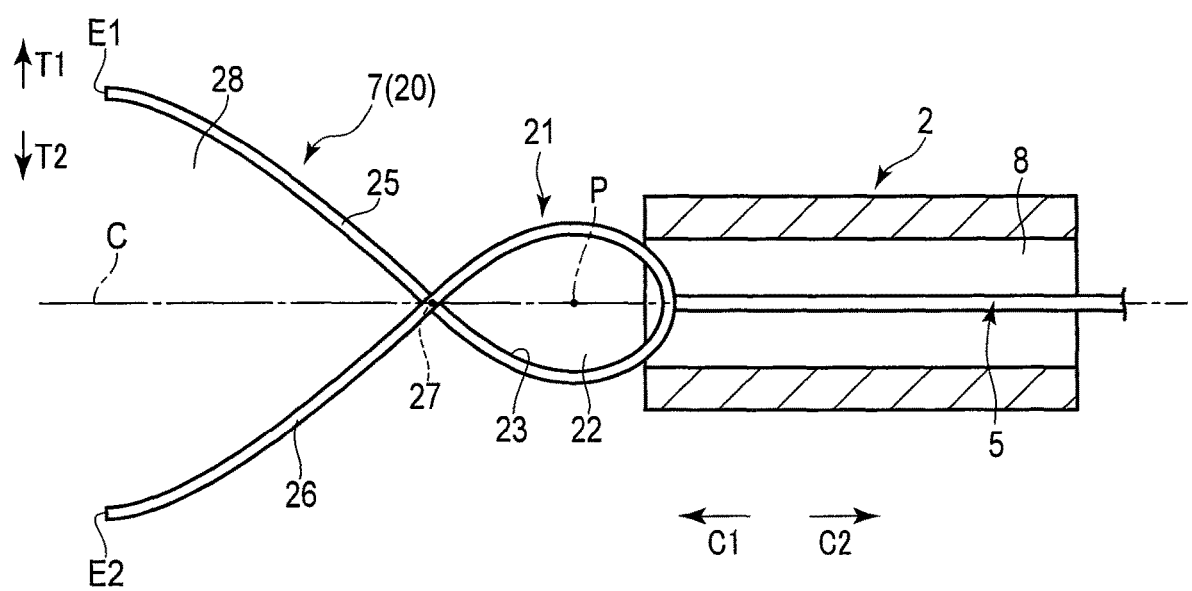
FIG. 2 is a schematic view of a locking member, a pressing tube, and a wire member according to the first embodiment, as viewed from one side in a width direction of the locking member.

FIGS. 2 to 4 each show the configuration of the locking member 7, the pressing tube 2 and the wire member 5. A width direction (direction of arrow W1 and arrow W2) of the locking member 7, which intersects with (is substantially perpendicular to) a direction along the longitudinal axis C, is defined. Also, a thickness direction (direction of arrow T1 and arrow T2) of the locking member 7, which intersects with (is substantially perpendicular to) a direction along the longitudinal axis C and also intersects with the (is substantially perpendicular to) width direction of the locking member 7, is defined. FIG. 2 shows a view seen from one side in the width direction of the locking member 7, and FIG. 3 shows a view seen from one side in the thickness direction of the locking member 7. Further, FIG. 4 shows a view from the distal side. In the present embodiment, the width direction of the locking member 7 is substantially parallel to the width direction of the constitution member 20 that forms the locking member 7. The thickness direction of the locking member 7 is substantially parallel to thickness direction of the constitution member 20 forming the locking member 7.

In the locking member 7 as shown in FIGS. 2 to 4, the constitution member 20 extends in a substantially a shape from one extension end E1 to another extension end E2, when viewed from the width direction. Furthermore, the locking member 7 includes a loop portion (loop) 21 formed in a ring shape (loop shape) when viewed from the width direction. In the loop portion 21, the constitution member 20 extends in a ring shape when viewed from the width direction of the locking member 7. The proximal end of the locking member 7 is constituted by the loop portion 21. In the present embodiment, the wire member 5 is connected to the loop portion 21. An inner space 22 surrounded by the loop portion 21 is formed in the locking member 7. The loop portion 21 has a central axis P, and the central axis P of the loop portion 21 passes through the inner space 22. In the present embodiment, the central axis P of the loop portion 21 is substantially parallel to the width direction of the locking member 7. The loop portion 21 includes a loop inner peripheral surface 23 which faces a side where the inner space 22 is located, in other words, a side towards the central axis P. The loop inner peripheral surface 23 is adjacent to the inner space 22. Note that FIGS. 2 to 4 indicate a state where the loop portion 21 protrudes from the distal end of the pressing tube 2 to the distal side.

In the locking member 7, a first extension 25 and a second extension 26 extend from the loop portion 21 to the distal side. Each of the extensions 25 and 26 is, for example, a plate section formed in a plate shape. The distal end of the first extension 25 is constituted by one extension end E1 of the constitution member 20, and the distal end of the second extension 26 is constituted by another extension end E2 of the constitution member 20. In the present embodiment, the distal end of the locking member 7 is constituted by the distal end of the first extension 25 and the distal end of the second extension 26. The distal end of the loop portion 21 is formed with an intersection portion (intersection) 27 where the pair of extensions 25 and 26 intersect when viewed from the width direction. In other words, the second extension 26 intersects with the first extension 25 at the intersection portion 27 of the distal end of the loop portion 21 when viewed from the width direction of the locking member 7. Therefore, the extensions 25 and 26 are protrusions that protrude from the intersection portion 27 to the distal side. In addition, on the distal side with respect to the intersection portion 27, the extensions 25 and 26 are spaced from each other in the thickness direction of the locking member 7, and a space 28 is formed between the extensions 25 and 26 in thickness direction of the locking member 7. Therefore, the distal end of the first extension 25 and the distal end of the second extension 26 are separate from each other in the thickness direction in the locking member 7.

Figure 5:
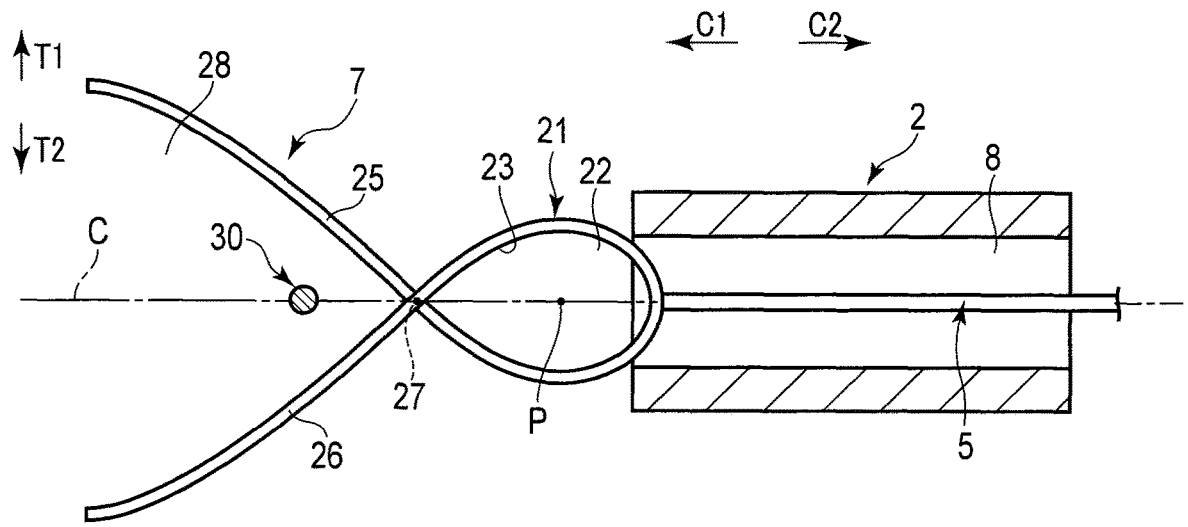
FIG. 5 is a schematic view of a state of a thread being inserted from the distal side into a space between a pair of extensions in the locking member according to the first embodiment, as viewed from one side in the width direction of the locking member.
Figure 6:
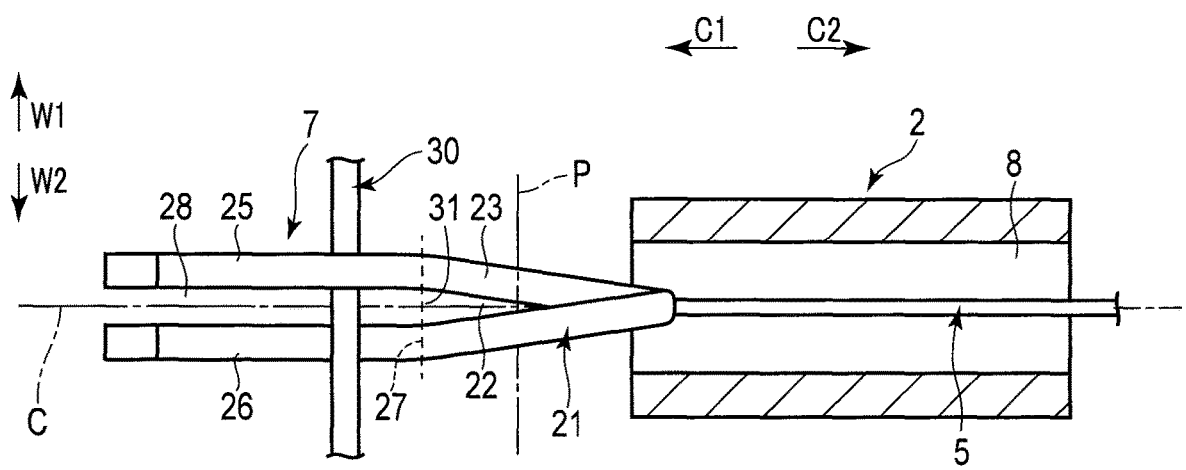
FIG. 6 is a schematic view of the state of the thread being inserted from the distal side into the space between the pair of extensions in the locking member according to the first embodiment, as viewed from one side in the thickness direction of the locking member.

Next, how to lock a thread 30 using the suture locking device 1 in treatment will be explained. The suture locking device 1, for example, is used to lock the thread 30 after suturing a treatment target such as biological tissues etc. by the thread 30. The thread 30 used has, for example, a suitable resilience, in other words, it may be a thread which is to a certain extent difficult to be bent. For using the suture locking device 1, the operator arranges the locking member 7 near the thread 30 with the loop portion 21 protruding from the distal end of the pressing tube 2 to the distal side, in other words, with the intersection portion 27 positioned on the distal side with respect to the distal end of the pressing tube 2. As shown in FIGS. 5 and 6, the suture locking device 1 is then moved so that the thread 30 is inserted from the distal side into the space 28 between the extensions 25 and 26. In that case, the thread 30 is inserted from between the distal end of the first extension 25 and the distal end of the second extension 26 into the space 28. In addition, the thread 30 here is allowed to extend along the width direction of the locking member 7, between the extensions 25 and 26. When the thread 30 has been inserted into the space 28 between the extensions 25 and 26, the operator moves the suture locking device 1 to the distal side with respect to the thread 30 until the thread 30 is positioned near the intersection portion 27 of the extensions 25 and 26. Note that FIG. 5 shows a view seen from one side in the width direction of the locking member 7 and FIG. 6 shows a view seen from one side in the thickness direction of the locking member 7.

Figure 7:
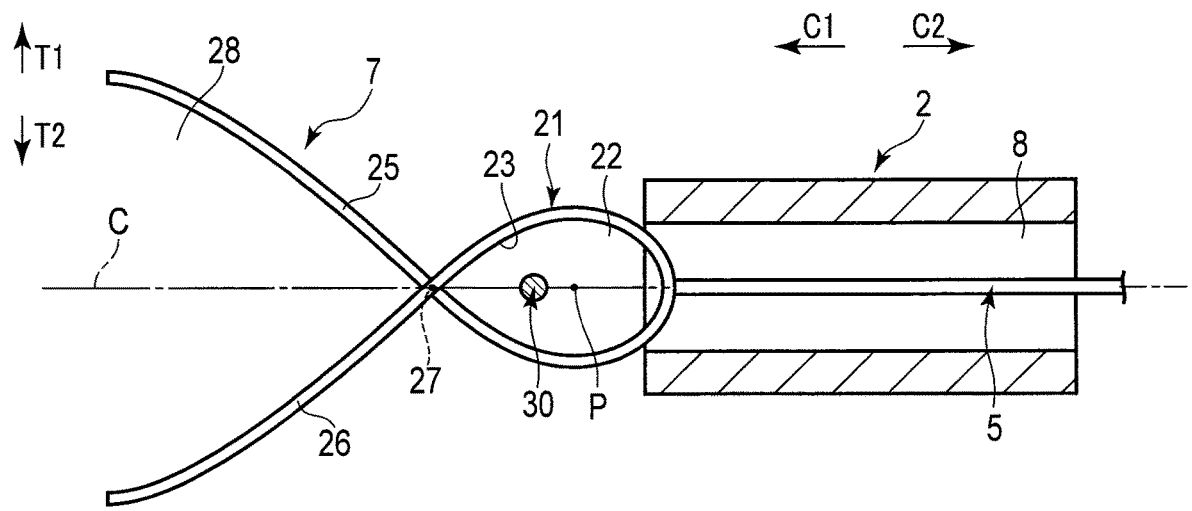
FIG. 7 is a schematic view of a state after the state shown in FIGS. 5 and 6, and shows the thread inserted into an inner space within a loop portion after passing through a gap in an intersection portion of the pair of extensions, as viewed from one side in the width direction of the locking member.
Figure 8:
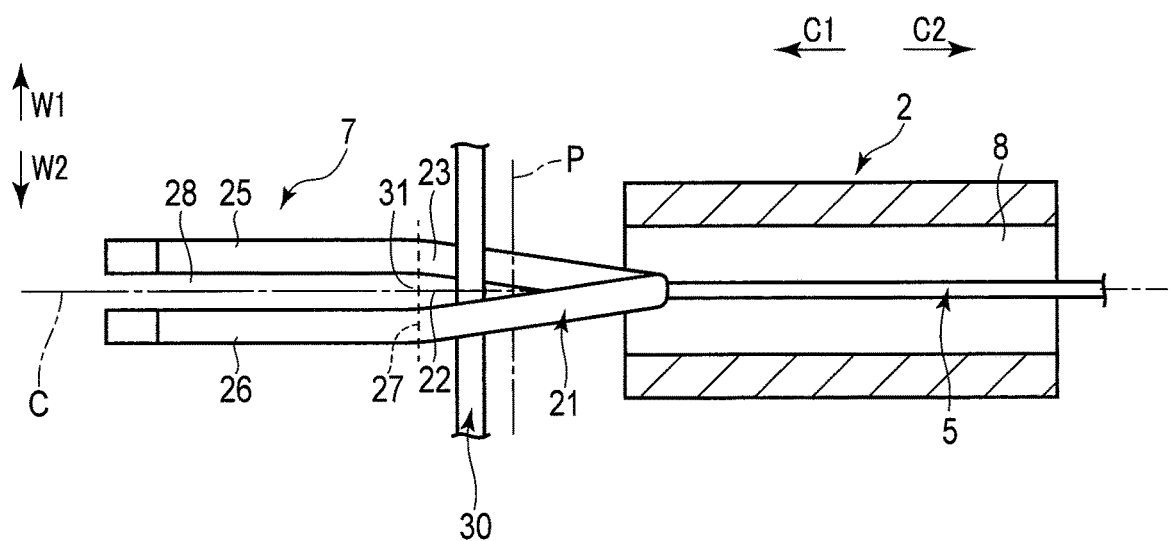
FIG. 8 is a schematic view of the state after the state shown in FIGS. 5 and 6, and shows the thread inserted into the inner space of the loop portion after passing through the gap in the intersection portion of the pair of extensions, as viewed from one side in the thickness direction of the locking member.

In a state where the loop portion 21 protrudes from the distal end of the pressing tube 2 to the distal side, a gap 31 is formed in the intersection portion 27 (distal end of the loop portion 21) between the extensions 25 and 26 in the width direction (refer to FIGS. 3, 4 and 6). When the thread 30 is positioned near the intersection portion 27 in the space 28, the operator rotates the locking member 7 around the longitudinal axis C. As shown in FIGS. 7 and 8, the thread 30 is thus inserted in the inner space 22 of the loop portion 21 from the distal side through the gap 31 in the intersection portion 27. By the above, the thread 30 now passes through the inner space 22.

The gap 31 in the intersection portion 27 may be larger or smaller than the outer diameter of the thread 30. When the gap 31 in the intersection portion 27 is larger than the outer diameter of the thread 30, the thread 30 can be easily inserted into the inner space 22 of the loop portion 21. However, in this case, it is preferred that the gap 31 is slightly larger than the outer diameter of the thread 30. When the gap 31 in the intersection portion 27 is smaller than the outer diameter of the thread 30, the thread 30 may elastically deform the intersection portion 27 and widens the gap 31 to as large as the outer diameter of the thread 30. By this, the thread 30 is inserted into the inner space 22 of the loop portion 21 through the gap 31.

In one embodiment, the locking member 7 may be adapted to be rotated together with the pressing tube 2, the coil sheath 3 and the wire member 5 around the longitudinal axis C upon rotating the above-mentioned held section (not shown) around the longitudinal axis C. In another embodiment, the locking member 7 may be adapted to be rotated around the longitudinal axis C with respect to the pressing tube 2 and the coil sheath 3 upon rotating the wire member 5 around the longitudinal axis C through the operation of the operation member (not shown) provided in the held section. In a state where the thread 30 is inserted in the inner space 22 of the loop portion 21, the thread 30 in the inner space 22 extends along the width direction of the locking member 7. Note that FIG. 7 shows a view seen from one side in the width direction of the locking member 7 and FIG. 8 shows a view seen from one side in the thickness direction of the locking member 7.

With the thread 30 passing through the inner space 22 of the loop portion 21, the operator pulls the wire member 5 to the proximal side by operating the operation member (not shown) provided in the aforementioned held section. By the above, the locking member 7 together with the wire member 5 moves to the proximal side relative to the pressing tube 2 and the coil sheath 3. Further, transition is made from a state where the loop portion 21 protrudes from the distal end of the pressing tube 2 to the distal side, that is, where the intersection portion 27 is positioned to the distal side with respect to the distal end of the pressing tube 2 as shown in FIGS. 7 and 8, to a state where the loop portion 21 is inserted into the hollow portion 8 in the pressing tube 2 from the distal side. Herewith, the loop portion 21 is arranged in the hollow portion 8 of the pressing tube 2. In the state where the loop portion 21 protrudes from the distal end of the pressing tube 2 to the distal side, the dimension of the loop portion 21 in the thickness direction of the locking member 7 is larger compared to the inner diameter of the hollow portion 8. Thus, the loop 21 is pressed to the inner side of the pressing tube 2, towards the longitudinal axis C, by the inner peripheral surface of the pressing tube 2 through the act of the loop portion 21 being inserted into the hollow portion 8. Accordingly, the locking member 7 including the loop portion 21 elastically deforms. Further, while the loop portion 21 is pressed to the inner peripheral side by the pressing tube 2, the operator further pulls the wire member 5 to the proximal side via the operation of the aforementioned operation member and moves the locking member 7 including the loop portion 21 to the proximal side in the hollow portion 8. Friction is generated between the loop portion 21 and the pressing tube 2, since the loop portion 21 contacts with the pressing tube 2.

Figure 9:
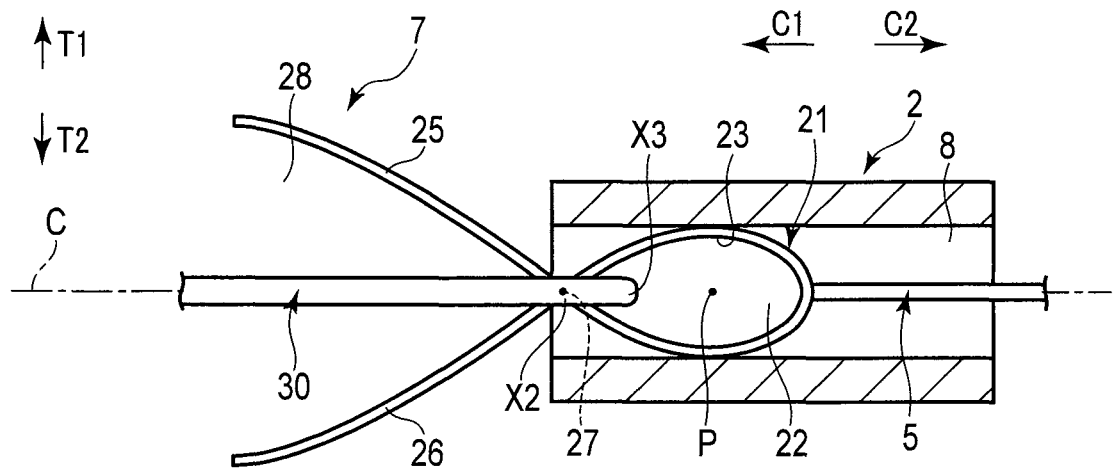
FIG. 9 is a schematic view of a state after the state shown in FIGS. 7 and 8, and shows the locking member inserted into a hollow portion of the pressing tube and the intersection portion of the pair of extensions positioned on a proximal side with respect to a distal end of the pressing tube, as viewed from one side in the width direction of the locking member.
Figure 10:
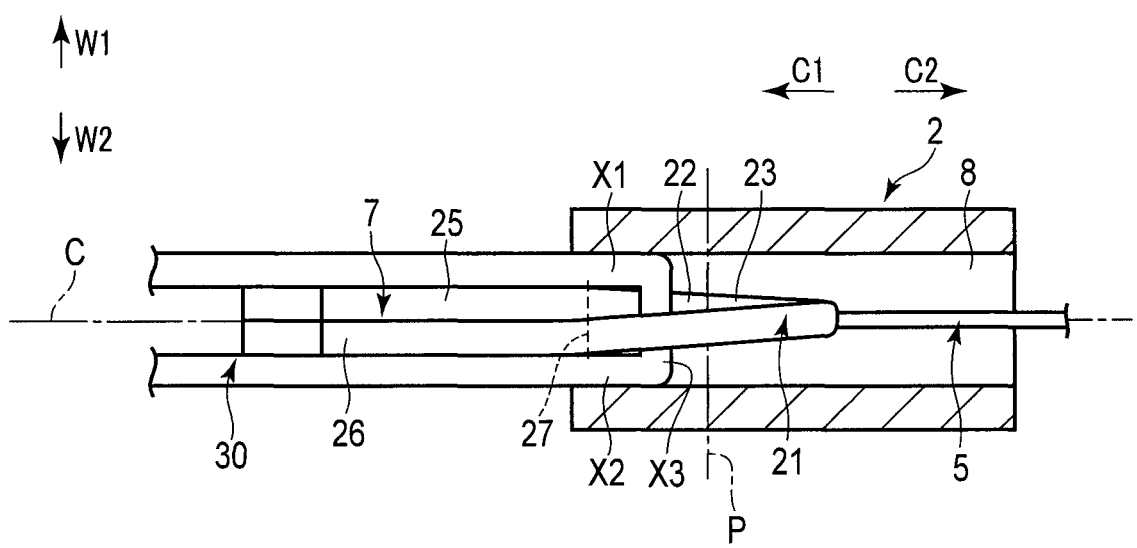
FIG. 10 is a schematic view of the state after the state shown in FIGS. 7 and 8, and shows the locking member inserted into the hollow portion of the pressing tube and the intersection portion of the pair of extensions positioned on the proximal side with respect to the distal end of the pressing tube, as viewed from one side in the thickness direction of the locking member.

As shown in FIGS. 9 and 10, when the locking member 7 is inserted into the hollow portion 8 to a state so that the intersection portion 27 is positioned on the proximal side with respect to the distal end of the pressing tube 2, the thread 30 is pulled to the hollow portion 8 of the pressing tube 2. If the thread 30 has a suitable resilience, the thread 30 can be pulled into the hollow portion 8 in a state of abutting the intersection portion 27 from the proximal side. In a state where the thread 30 has been pulled in the hollow portion 8 of the pressing tube 2, the thread 30 in the hollow portion 8 extends in substantially a U-shape wrapped in the inner space 22 of the loop portion 21. That is, the part of the thread 30 pulled into the hollow portion 8 extends towards the proximal side from the distal opening of the hollow portion 8 to the inner space 22, and then passes through the inner space 22 of the loop portion 21 and extends toward the distal side from the inner space 22 to the distal opening of the hollow portion 8. If the thread 30 has a suitable resilience, the thread 30 can maintain, while part thereof is pulled in the hollow portion 8, the abutment on the inner peripheral surface of the pressing tube 2 at the distal opening of the hollow portion 8. Note that FIG. 9 shows a view seen from one side in the width direction of the locking member 7 and FIG. 10 shows a view seen from one side in the thickness direction of the locking member 7.

When the thread 30 is pulled into the hollow portion 8, portions X1 and X2 of the thread 30 extending along the longitudinal axis C from the distal opening to the inner space 22 are interposed between the inner peripheral surface of the pressing tube 2 and the locking member 7. Thus, the portions X1 and X2 of the thread 30 contact the pressing tube 2 and the locking member 7 and are held between the pressing tube 2 and the locking member 7 with a light force. The portions X1 and X2 of the thread 30 are guided along the longitudinal axis C by being interposed between the inner peripheral surface of the pressing tube 2 and the locking member 7. Herewith, the part of the thread 30 pulled into the hollow portion 8 is biased to a state of extending in substantially a U-shape wrapped in the inner space 22. The portions X1 and X2 of the thread 30, interposed between the pressing tube 2 and the locking member 7, are held with a light force so they can be slid in a direction along the longitudinal axis C with respect to the pressing tube 2 and the locking member 7.

Thus, when the loop portion 21 begins to be inserted into the hollow portion (hollow) 8 of the pressing tube 2, the contact area between the locking member 7 and the inner peripheral surface of the pressing tube 2 increases as the locking member 7 moves towards the proximal side in the hollow portion 8. Therefore, after the loop portion 21 begins to be inserted into the hollow portion 8 of the pressing tube 2, the friction force between the locking member 7 and the pressing tube 2 increases as the locking member 7 moves towards the proximal side in the hollow portion 8.

After the state shown in FIGS. 9 and 10 of the intersection portion 27 being positioned on the proximal side with respect to the distal end of the pressing tube 2, when the locking member 7 is further moved to the proximal side in the hollow portion 8, parts of the extensions 25 and 26 located on the distal side from the intersection portion 27 are pressed to the inner peripheral side by the inner peripheral surface of the pressing tube 2. Further, after the parts of the extensions 25 and 26 on the distal side with respect to the intersection portion 27 begin to be pressed by the pressing tube 2, the extensions 25 and 26 approach each other at the parts on the distal side from the intersection portion 27 and the space 28 between the extensions 25 and 26 becomes small, in conjunction with the locking member 7 moving towards the proximal side of the hollow portion 8. When the extensions 25 and 26 become close to each other at the parts on the distal side with respect to the intersection portion 27, the loop portion 21 elastically deforms in the direction where the dimension in the thickness direction of the locking member 7 increases. Thus, after the parts of the extensions 25 and 26 located on the distal side from the intersection portion 27 begin to be pressed by the pressing tube 2, the outward pressing force from the loop portion 21 to the pressing tube 2 increases as the locking member 7 moves toward the proximal side in the hollow portion 8. Therefore, after the parts of the extensions 25 and 26 located on the distal side from the intersection portion 27 begin to be pressed by the pressing tube 2, the increase in the friction force between the locking member 7 and the pressing tube 2 that originated from the movement of the locking member 7 to the proximal side in the hollow portion 8 becomes rapid.

Figure 11:
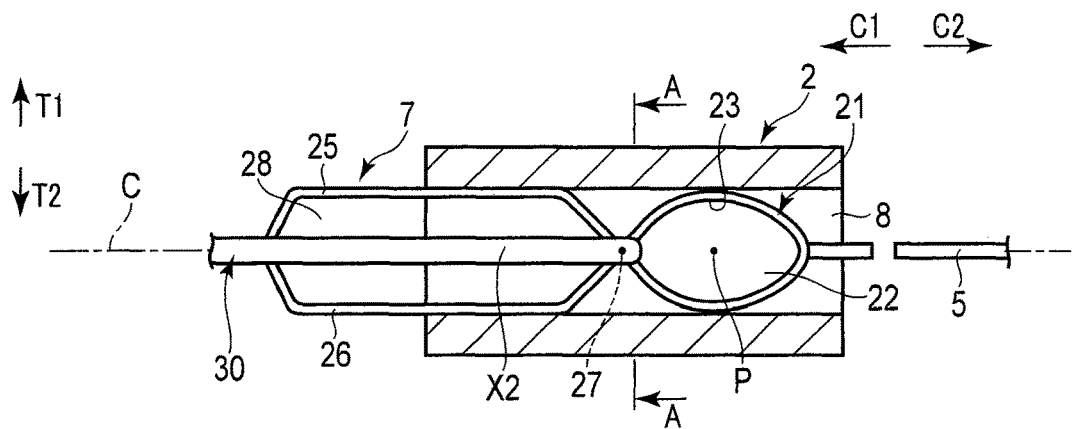
FIG. 11 is a schematic view of a state after the state shown in FIGS. 9 and 10, and shows that the locking member is further moved to the proximal side in the hollow portion, and the wire member and the locking member are separated, as viewed from one side in the width direction of the locking member.
Figure 12:
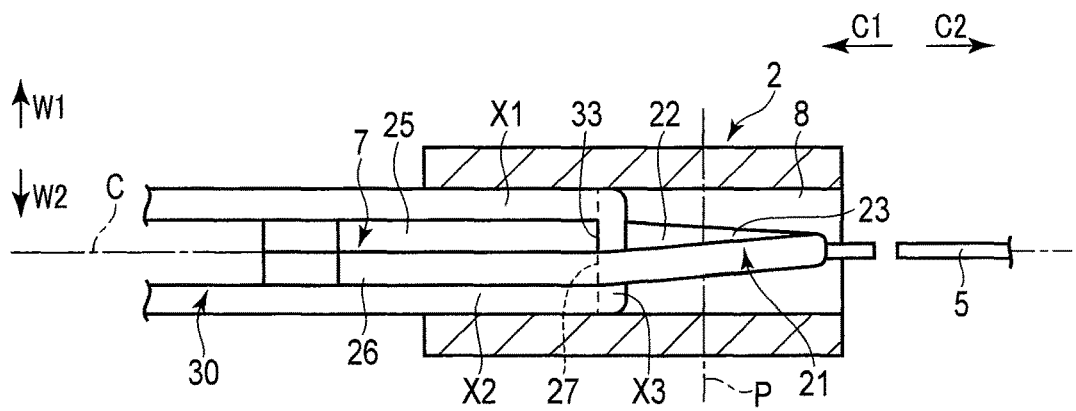
FIG. 12 is a schematic view of the state after the state shown in FIGS. 9 and 10, and shows that the locking member is further moved to the proximal side in the hollow portion, and the wire member and the locking member are separated, as viewed from one side in the thickness direction of the locking member.

When the locking member 7 moves to the proximal side in the hollow portion 8 to the state shown in FIGS. 11 and 12, the friction force between the locking member 7 and the pressing tube 2 becomes a predetermined magnitude or greater. A tensile force exerting in the direction along the longitudinal axis C is present between the wire member 5 and the locking member 7, and this force increases when the friction between the locking member 7 and the pressing tube 2 increases. Therefore, in the state shown in FIGS. 11 and 12 where the friction force between the locking member and the pressing tube 2 reaches or exceeds a predetermined magnitude, the tensile force in the direction along the longitudinal axis C between the wire member 5 and the locking member 7 becomes a predetermined size or greater, so that the wire member 5 is disconnected at the distal portion of the wire member 5 by the tensile force. The connection of the wire member 5 to the locking member 7 is thus broken. By separating the wire member 5 from the locking member 7, the pressing tube 2 separates from the coil sheath 3. As described above, in the present embodiment, the inner peripheral surface of the pressing tube 2 and the locking member 7 function as a separator configured to break a connection of the wire member 5 to the locking member 7. Note that FIG. 11 shows a view seen from one side in the width direction of the locking member 7, and FIG. 12 shows a view seen from one side in the thickness direction of the locking member 7.

As described above, after the loop portion 21 begins to be inserted into the hollow portion 8 of the pressing tube 2, the friction force between the locking member 7 and the pressing tube 2 increases as the locking member 7 moves towards the proximal side in the hollow portion 8. In the state shown in FIGS. 11 and 12, the friction force between the locking member 7 and the pressing tube 2 comes to be a predetermined magnitude or greater. Thus, when the locking member 7 moves towards the proximal side in the hollow portion 8 to the state as shown in FIGS. 11 and 12, the locking member 7 in the hollow portion 8 is fixed to the pressing tube 2 by the friction between the inner peripheral surface of the pressing tube 2 and the locking member 7.

In addition, when the intersection portion 27 is inserted into the hollow portion 8 and the thread 30 is pulled into the hollow portion 8, a part of the thread 30 that extends in substantially a U-shape in the hollow portion 8 is applied a tensile force toward the distal side. Therefore, a portion X3 of the thread 30 extended in the inner space 22 of the loop portion 21 is pulled from the proximal side towards the intersection portion 27. Further, when the locking member 7 including the loop portion 21 is elastically deformed by the inward pressing from the pressing tube 2, the gap 31 in the intersection portion 27 closes or decreases to a size at which it is incapable for the thread 30 to pass through. Thus, even if the thread 30 is pulled towards the intersection portion 27 in the inner space 22 of the loop portion 21 by the tensile force, the situation in which the thread 30 falls out through the gap 31 from the inner space 22 can be prevented.

Figure 13:
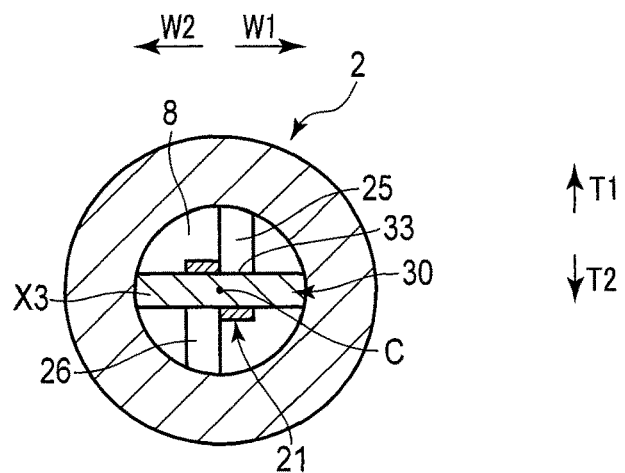
FIG. 13 is a cross-sectional view schematically showing an A-A cross section of FIG. 11.

FIG. 13 shows an A-A cross section of FIG. 11. As shown in FIGS. 11 to 13, when the locking member 7 is elastically deformed as described above due to the pressing tube 2 pressing to the inner peripheral side, and when the thread 30 is pulled towards the intersection portion 27 in the inner space 22, the thread 30 abuts the loop inner peripheral surface 23 (extensions 25 and 26) of the loop portion 21 from the proximal side. In other words, the loop inner peripheral surface 23 allows the thread 30 to form an abutting part 33 abutting from the proximal side. On the loop inner peripheral surface 23, the abutting part 33 of the thread 30 is formed along the width direction of the locking member 7, and the abutting part 33 is formed over a predetermined dimension range in the width direction of the locking member 7. Since the thread 30 abuts the loop inner peripheral surface 23, friction is generated between the abutting part 33 and the loop inner peripheral surface 23. The abutting part 33 is retained in the loop portion 21 by the friction between the abutting part 33 and the loop inner peripheral surface 23. The thread 30 is thereby locked to the locking member 7 including the loop portion 21. Further, when the locking member 7 moves towards the proximal side in the hollow portion 8 to the state as shown in FIGS. 11 and 12, the locking member 7 is fixed to the pressing tube 2 as described above. Therefore, in the state shown in FIGS. 11 and 12, the thread 30 is locked to the pressing tube 2.

When the intersection portion 27 is inserted into the hollow portion 8 and parts of the extensions 25 and 26 located on the distal side from the intersection portion 27 are pressed to the inner peripheral side by the inner peripheral surface of the pressing tube 2, the parts of the extensions 25 and 26 located on the distal side from the intersection portion 27 move closer to each other as described above. Thus, in one embodiment, when the locking member 7 moves towards the proximal side in the hollow portion 8 to the state as shown in the FIGS. 11 and 12, the thread 30 may be interposed between the extensions 25 and 26 at the parts located on the distal side from the intersection portion 27.

As described above, in the present embodiment, the thread 30 is pulled from the proximal side towards the intersection portion 27 in the inner space 22 of the loop portion 21, by inserting the loop portion 21 along the longitudinal axis C from the distal side into the hollow portion 8 of the pressing tube 2 with the thread 30 passing through the inner space 22 of the loop portion 21. Thus, the thread 30 abuts the loop inner peripheral surface 23 (extensions 25 and 26) of the loop portion 21 from the proximal side, and the abutting part 33 of the thread 30 is retained in the loop portion 21 by the friction between the abutting part 33 and the loop inner peripheral surface 23, so that the thread 30 is locked to the locking member 7 and the pressing tube 2. In the present embodiment, since the thread 30 is locked as described above, the locking force of the thread 30, in other words, the friction between the thread 30 and the loop inner peripheral surface 23, is not affected by the dimension tolerance of the members such as the locking member 7 and the pressing tube 2 etc. or by the dimension tolerance of the thread 30. Therefore, the thread 30 can be locked to the locking member 7 with a stable locking force regardless of the dimension tolerances of each component or the thread 30. Thus, a stable locking force for the thread 30 can be secured. Further, since the thread 30 is fixed by a stable locking force, the locking force for the thread 30 can be prevented from becoming excessively large, and it can also effectively prevent the deformation and disconnection etc. of the thread 30.

Further, the foregoing example has assumed an instance of arranging the thread 30 from the distal side to the inner space 22 surrounded by the loop portion 21, through the space 28 between the extensions 25 and 26 and the gap 31 in the intersection portion 27; however, this is not a limitation. In one exemplary use, the thread 30 may be directly arranged in the inner space 22 surrounded by the loop portion 21, from the direction intersecting with the longitudinal axis C, e.g., the width direction etc. of the locking member 7 that is substantially perpendicular to the longitudinal axis C.

Modifications

In the first embodiment, a cross-sectional shape of the hollow portion 8 that is substantially perpendicular to the longitudinal axis C has a substantially circular shape; however, this is not a limitation. For example, according to a first modification shown in FIG. 14, an inner peripheral surface of the pressing tube 2 forming the hollow portion 8 includes flat surfaces 41A and 41B. In the present modification, the part other than the flat surfaces 41A and 41B in the inner peripheral surface of the pressing tube 2 is formed as an arc-shape curved surface in a cross section substantially perpendicular to the longitudinal axis C. Furthermore, according to a second modification shown in FIG. 15, the inner peripheral surface of the pressing tube 2 is formed by the flat surfaces 41A to 41D. In this case, the cross-sectional shape of the hollow portion 8 that is substantially perpendicular to the longitudinal axis C is formed in a substantially square shape. Both in the first modification and the second modification, a flat surface (41A, 41B; 41A to 41D) is provided so that the locking member 7 can be further suitably elastically deformed by the flat surface (41A, 41B; 41A to 41D) pressing inwardly upon insertion of the loop portion 21 into the hollow portion 8. Therefore, the gap 31 in the intersection portion 27 further appropriately closes, or is reduced to a size that is incapable for the thread 30 to pass through.

Further, according to a third modification shown in FIG. 16, a tapered surface 42 that gradually reduces the inner diameter of the hollow portion 8 from the proximal side to the distal side is provided on the inner peripheral surface of the pressing tube 2. In the present modification, after the loop portion 21 is inserted into the hollow portion 8, the locking member 7 including the loop portion 21 is hardly slip out from the hollow portion 8 to the distal side. For example, in a state where the thread 30 is pulled into the hollow portion 8, even if the tensile force toward the distal side affecting the thread 30 increases, this effectively prevents the locking member 7 from slipping out from the hollow portion 8 to the distal side.

Figure 17:
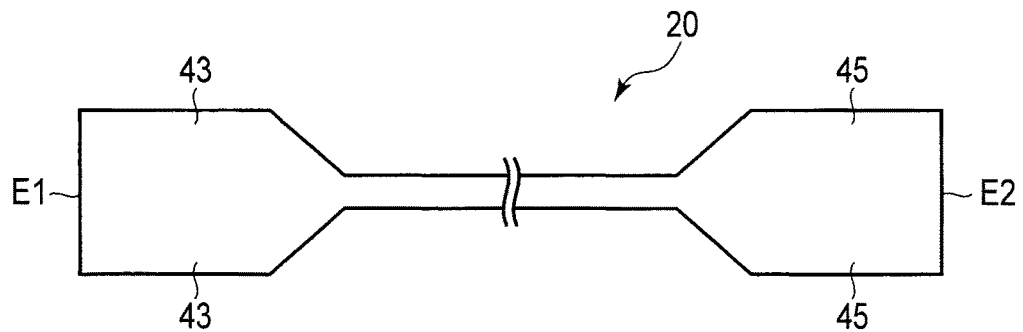
FIG. 17 is a schematic view showing a constitution member forming a locking member according to a fourth modification.
Figure 18:
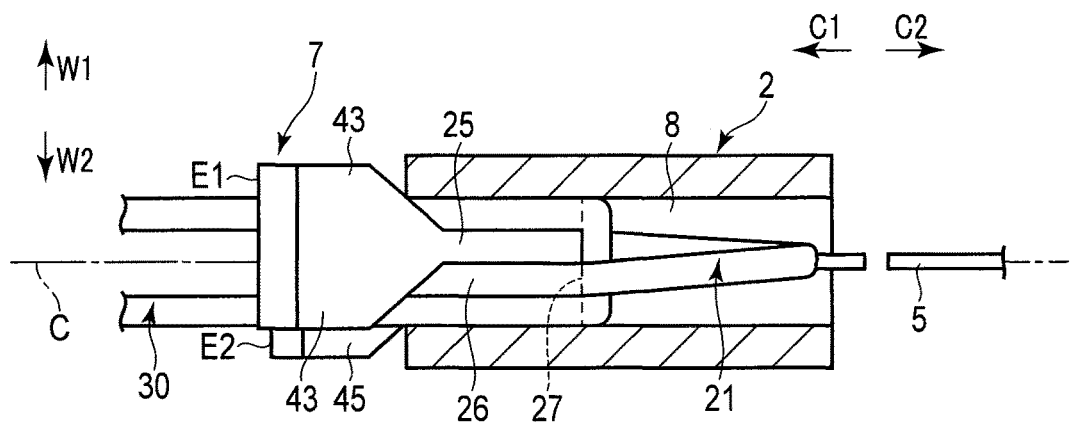
FIG. 18 is a schematic view of a state where the locking member according to the fourth modification moves to a proximal side in the hollow portion of the pressing tube, and the wire member and the locking member are separated, as viewed from one side in the thickness direction of the locking member.

According to a fourth modification shown in FIGS. 17 and 18, the constitution member 20, which forms the locking member 7, is provided with protrusions 43 and 45 which are tabs (ear portions) protruding in the width direction of the constitution member 20. The protrusion 43 is formed on one extension end E1 of the constitution member 20 and in its vicinity, and the protrusion 45 is formed on another extension end E2 of the constitution member 20 and in its vicinity. Courtesy of the protrusions 43 and 45, the dimensions in the width direction of the constitution member 20 at the extension ends E1 and E2 and in their vicinities are made larger. In the locking member 7, the protrusions 43 and 45 are provided on the distal side with respect to the intersection portion 27. Further, the protrusion 43 is provided on the distal portion of the first extension 25 and forms the distal end of the first extension 25. In addition, the protrusion 45 is provided on the distal portion of the second extension 26 and forms the distal end of the second extension 26.

In the present modification, when the loop portion 21 is inserted into the hollow portion 8 of the pressing tube 2, and when the locking member 7 moves to a predetermined position toward the proximal side in the hollow portion 8, the proximal end of the protrusion 43 and the proximal end of the protrusion 45 abut the distal surface of the pressing tube 2 from the distal side. Thus, a part of the first extension 25 located on the distal side from the proximal end of the protrusion 43 and a part of the second extension 26 located on the distal side from the proximal end of the protrusion 45 are not inserted into the hollow portion 8. Courtesy of the protrusions 43 and 45 abutting the distal surface of the pressing tube 2, a reactive force to the protrusions 43 and 45 from the pressing tube 2 affects the tensile force in the direction along the longitudinal axis C between the wire member 5 and the locking member 7, in addition to the friction force between the locking member 7 and the inner peripheral surface of the pressing tube 2. Therefore, in the present modification, when the locking member 7 moves to a predetermined position toward the proximal side in the hollow portion 8, the tensile force of a predetermined magnitude or greater can act reliably between the locking member 7 and the wire member 5. Therefore, when the locking member 7 moves to a predetermined position toward the proximal side in the hollow portion 8, the connection of the wire member 5 to the locking member 7 is reliably broken. As such, in the present modification, the protrusions 43 and 45 of the locking member 7 function as a separator configured to break a connection of the wire member 5 to the locking member 7.

Figure 19:
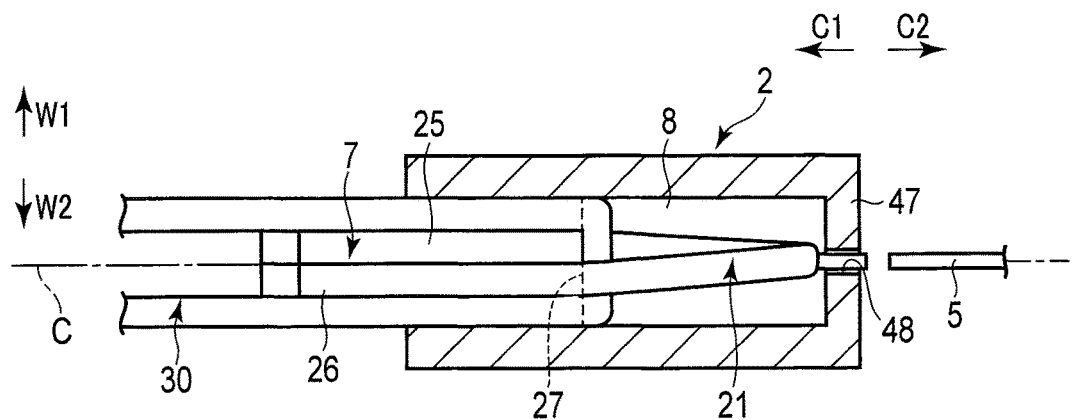
FIG. 19 is a schematic view of a state where a locking member according to a fifth modification is moved in the hollow portion to the proximal side, and the wire member and the locking member are separated, as viewed from one side in the thickness direction of the locking member.

According to a fifth modification shown in FIG. 19, the proximal portion of the hollow portion 8 of the pressing tube 2 is provided with a protrusion 47 whereby the inner peripheral surface of the pressing tube 2 protrudes inwardly. In the present modification, the protrusion 47 is formed over an entire periphery around the longitudinal axis C. Thus, the proximal portion of the hollow portion 8 is formed with a hole 48 surrounded by the protrusion 47 over the entire periphery around the longitudinal axis C. The cross-sectional area of the hole 48 that is substantially perpendicular to the longitudinal axis C is of a size that allows the wire member 5 to be inserted. In addition, the cross-sectional area of the hole 48 that is substantially perpendicular to the longitudinal axis C is of a size that does not permit the locking member 7 (loop portion 21) to pass through.

In the present modification, when the loop portion 21 is inserted into the hollow portion 8 of the pressing tube 2, and when the locking member 7 moves to a predetermined position toward the proximal side in the hollow portion 8, the loop portion 21 abuts the protrusion 47 of the pressing tube 2 from the distal side. Thus, the proximal end of the locking member 7 does not move to the proximal side from the distal end of the protrusion 47. Courtesy of the locking member 7 abutting the protrusion 47, a reactive force to the locking member 7 from the protrusion 47 affects the tensile force in the direction along the longitudinal axis C between the wire member 5 and the locking member 7, in addition to the friction force between the locking member 7 and the inner peripheral surface of the pressing tube 2. Therefore, in the present modification, when the locking member 7 moves to a predetermined position toward the proximal side in the hollow portion 8, the tensile force of a predetermined magnitude or greater can act reliably between the locking member 7 and the wire member 5. Therefore, when the locking member 7 moves to a predetermined position toward the proximal side in the hollow portion 8, the connection of the wire member 5 to the locking member 7 is reliably broken. As such, in the present modification, the protrusion 47 of the pressing tube 2 functions as a separator configured to break a connection of the wire member 5 to the locking member 7.

Further, in the foregoing embodiments, etc., the wire member 5 is directly connected to the locking member 7; however, this is not a limitation. In one modification, a connection member (not shown) may be provided between the loop portion 21 of the locking member 7 and the wire member 5. In this case, one end of the connection member is connected to the loop portion 21 of the locking member 7 and another end of the connection member is connected to the wire member 5. Note that one end of the connection member may be removably connected to the loop portion 21 of the locking member 7, and another end of the connection member may be removably connected to the wire member 5. That is, in such a modification, the wire member 5 is indirectly connected to the locking member 7 via the connection member. In that case, upon pulling the wire member 5 to the proximal side, the wire member 5 and the loop portion 21 of the locking member 7 can be separated from each other by the breaking etc. of one end or another end of the connection member.

The following notes the additional features of the present invention.

Additional Note 1

A method of locking a thread using a suture locking device, the suture locking device comprising: a pressing tube which extends along a longitudinal axis from a proximal side to a distal side and inside which a hollow portion is formed; a locking member formed from a constitution member having elasticity and extending in an α-shape when viewed from a width direction intersecting with a direction along the longitudinal axis; a loop portion forming a proximal end of the locking member and formed in a ring-shape when viewed from the width direction; a first extension extending from the loop portion to the distal side in the locking member and including a distal end formed by one extension end of the constitution member; and a second extension extending from the loop portion to the distal side in the locking member, and including a distal end formed by another extension end of the constitution member, the second extension forming an intersection portion intersecting with the first extension at a distal end of the loop portion when viewed from the width direction, the method comprising:

inserting the thread into an inner space surrounded by the loop portion with the loop portion protruding from a distal end of the pressing tube to the distal side;

inserting the loop portion into the hollow portion of the pressing tube from the distal side towards the proximal side along the longitudinal axis with the thread inserted into the inner space of the loop portion, and pressing the loop portion to an inner peripheral side of the pressing tube towards the longitudinal axis by the pressing tube; and moving the locking member to the proximal side in the hollow portion with the thread inserted into the inner space of the loop portion, and pulling the thread from the proximal side towards the intersection portion in the inner space of the loop portion.

Additional Note 2

A method according to additional note 1, wherein the inserting the thread into the inner space includes inserting the thread from the distal side into the inner space of the loop portion, through a gap formed between the first extension and the second extension in the width direction in the intersection portion, by rotating the locking member around the longitudinal axis with the thread positioned on the distal side with respect to the intersection portion.

Additional Note 3

A method according to additional note 2, wherein the inserting the loop portion into the hollow portion of the pressing tube includes closing or reducing the gap in the intersection portion by elastically deforming the loop portion due to a pressing from the pressing tube to the inner peripheral side, so as to prevent the thread from slipping out of the inner space.

Additional Note 4

A method according to additional note 1, wherein the moving the locking member to the proximal side in the hollow portion includes pulling the thread into the hollow portion, and biasing the thread between a distal opening of the hollow portion and the inner space so that the thread extends in a U-shape that is wrapped in the inner space.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A suture locking device comprising:
   a pressing tube extending along a longitudinal axis from a proximal side to a distal side, a hollow portion being formed inside the pressing tube; and
   a locking member including:
   a loop portion forming a proximal end of the locking member, the loop portion being configured to be inserted into the hollow portion from the distal side towards the proximal side along the longitudinal axis with a thread being inserted through an inner space surrounded by the loop portion;
   a first extension extending distally from the loop portion;
   second extension extending distally from the loop portion;
   an intersection portion where the first extension and the second extension intersect at a distal end of the loop portion when viewed from a width direction intersecting with a direction along the longitudinal axis; and
   a gap formed at the intersection portion between the first extension and the second extension, the gap being formed in the width direction when the loop portion protrudes from a distal end of the pressing tube to the distal side, the locking member being configured such that the gap is closed or reduced to prevent the thread from coming out from the inner space when the loop portion is deformed by an inward pressing from the pressing tube.

2. The suture locking device according to claim 1, wherein
the loop portion includes a loop inner peripheral surface facing a side where the inner space is located,
the pressing tube is configured to press the loop portion to the inner peripheral side and the thread is pulled towards the intersection portion in the inner space so that the thread abuts the loop inner peripheral surface from the proximal side,
an abutting part of the thread to abut the loop inner peripheral surface is formed along the width direction, and
the loop portion retains the abutting part to the loop inner peripheral surface.

3. The suture locking device according to claim 1, wherein
the thread is inserted into the inner space of the loop portion proximally through the gap in the intersection portion when the loop portion protrudes from the distal end of the pressing tube to the distal side.

4. The suture locking device according to claim 1, wherein the locking member is configured to be elastically deformed by the loop portion being inserted into the hollow portion of the pressing tube and by receiving the inward pressing from the pressing tube to lock the locking member in the hollow portion of the pressing tube.

5. The suture locking device according to claim 1, further comprising:
a wire member including a distal end connected to the locking member, the wire member being configured to insert the loop portion into the hollow portion of the pressing tube by being pulled proximally into the distal end of the pressing tube.

6. The suture locking device according to claim 5, further comprising:
a separator provided on any of the locking member and the pressing tube, the separator being configured to separate the wire member from the locking member when the locking member is positioned in the hollow portion of the pressing tube.

7. The suture locking device according to claim 1, wherein the pressing tube is configured to press the loop portion to an inner peripheral side of the pressing tube to lock the thread to the loop portion.

8. The suture locking device according to claim 1, wherein
the loop portion is formed in an α-shape when viewed from the width direction,
the first extension includes a distal end formed by a first extension end of the locking member, and
the second extension includes a distal end formed by a second extension end of the locking member.

9. A method of locking a thread using a suture locking device, the suture locking device including,
a pressing tube extending along a longitudinal direction from a proximal side to a distal side, a hollow portion being formed inside the pressing tube,
a locking member configured to be inserted in the hollow portion, the locking member including a first extension, a second extension, and an intersection portion where the first extension and the second extension intersect when viewed from a width direction intersecting with the longitudinal direction,
the method comprising:
disposing the thread distally with respect to the intersection portion in a space between the first and second extentions;
disposing the thread proximally with respect to the intersection portion with the suture locking device being inserted into a body cavity and with the intersection portion protruding from a distal end of the pressing tube toward the distal side;
proximally inserting the intersection portion and the thread into the hollow portion of the pressing tube with the thread being disposed proximally with respect to the intersection portion to lock the thread to the locking member; and
retaining the suture locking device in a biological tissue with the thread being locked to the locking member.

10. The method according to claim 9, wherein
the locking member further includes a gap formed between the first extension and the second extension in the width direction in the intersection portion,
the method further comprising:
proximally inserting the intersection portion and the thread into the hollow portion of the pressing tube with the thread being disposed proximally with respect to the intersection portion to close or reduce the gap; and
locking the thread to the locking member by closing or reducing the gap.

11. The method according to claim 9, further comprising
retaining the suture locking device in a biological tissue with the locking member and the thread protruding distally from the distal end of the pressing tube.

12. The method according to claim 9, further comprising
the locking member further includes a loop portion forming a proximal end of the locking member, the loop portion being formed in a ring-shape when viewed from the width direction, the loop portion being located on the proximal side with respect to the intersection portion,
the method further comprising:
disposing the thread in an inner space of the loop portion with the suture locking device being inserted into the body cavity and with the intersection portion protruding from the distal end of the pressing tube.

* * * * *